United States Patent [19]
Sansoni

[11] Patent Number: 5,526,806
[45] Date of Patent: Jun. 18, 1996

[54] NON-INVASIVE NASAL CANNULA

[76] Inventor: Jean Sansoni, 511 Buckman Dr., Hatboro, Pa. 19040

[21] Appl. No.: 416,189

[22] Filed: Apr. 4, 1995

[51] Int. Cl.$^6$ .................................................. A61M 15/08
[52] U.S. Cl. ............................ 128/207.18; 128/207.13; 128/206.11; 128/206.18
[58] Field of Search ......................... 128/207.18, 207.13, 128/204.18, 911, 912, 206.18, 204.12, 206.11

[56] References Cited

U.S. PATENT DOCUMENTS

| | | | |
|---|---|---|---|
| 4,106,505 | 8/1978 | Salter et al. | 128/207.18 |
| 4,216,769 | 8/1980 | Grimes | 128/207.13 |
| 4,354,488 | 10/1982 | Bastos | 128/207.13 |
| 4,406,283 | 9/1983 | Bir | 128/207.18 |
| 5,188,101 | 2/1993 | Tumolo | 128/207.18 |
| 5,271,391 | 12/1993 | Graves | 128/207.18 |
| 5,335,656 | 8/1994 | Bowe et al. | 128/207.18 |

*Primary Examiner*—Edgar S. Burr
*Assistant Examiner*—V. Srivastava
*Attorney, Agent, or Firm*—Howson and Howson

[57] ABSTRACT

An improved non-invasive nasal cannula having an enlarged orifice for delivering a stream of oxygen to a patient's nasal passages. The cannula structure has means for directing substantially the entire stream of oxygen toward the patient's nasal passages and has means for maintaining it in a proper position on the patient.

20 Claims, 2 Drawing Sheets

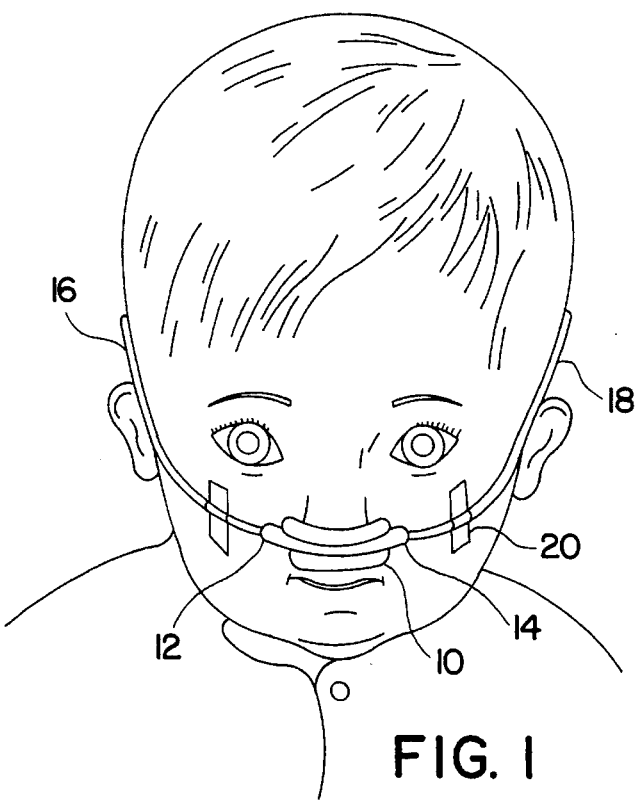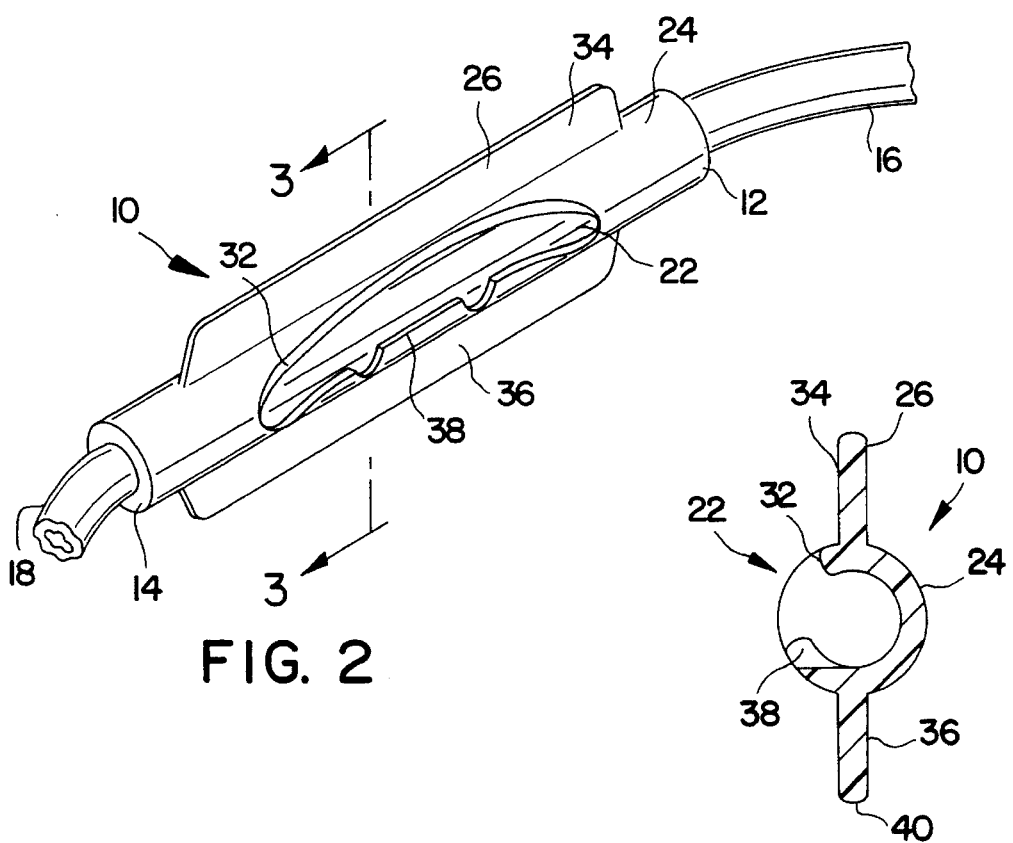

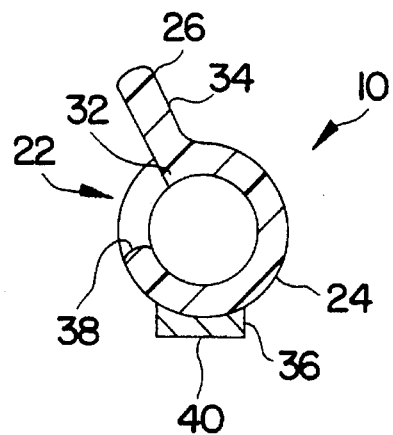
FIG. 4
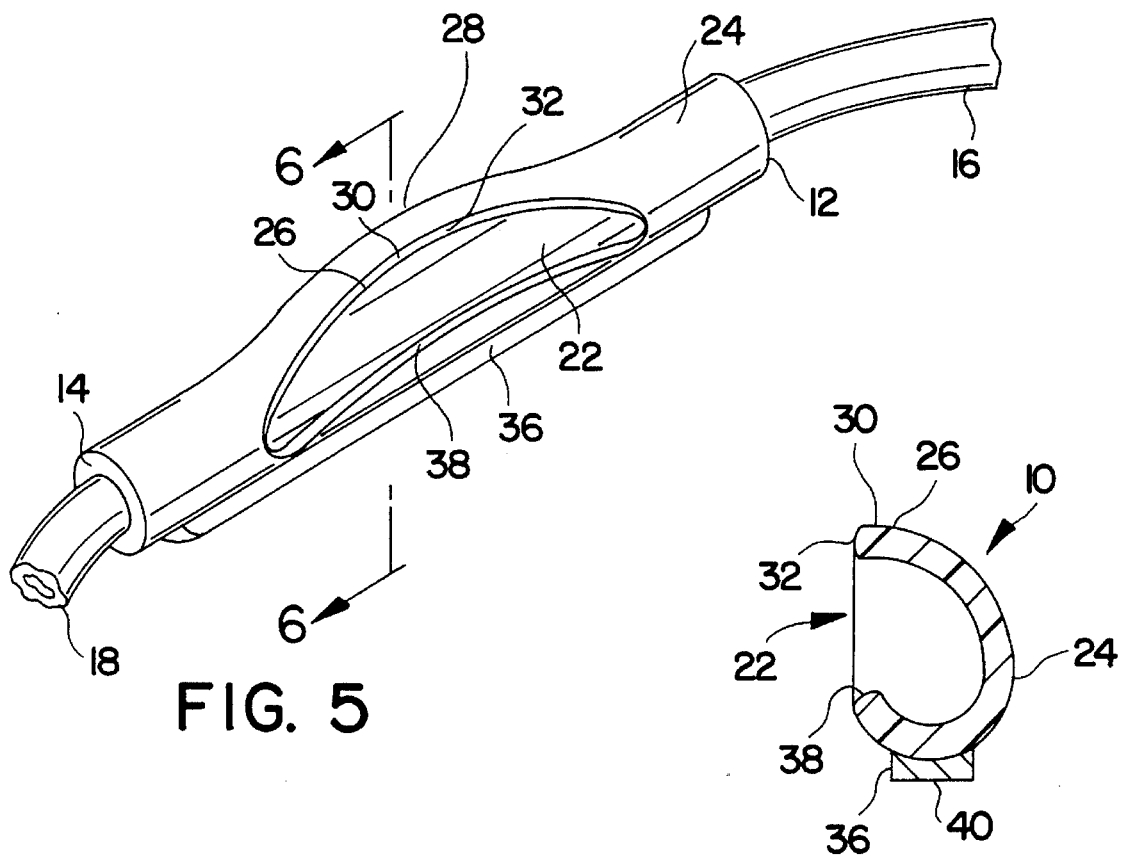
FIG. 5
FIG. 6

NON-INVASIVE NASAL CANNULA

FIELD OF THE INVENTION

The present invention relates to a cannula for use in delivering a stream of oxygen to a patient's nasal passages, and more particularly the present invention relates to a non-invasive nasal cannula having means for directing substantially the entire oxygen stream toward the patient's nasal passages.

BACKGROUND OF THE INVENTION

In the field of medicine, a patient may often require the administration of a pure supply of oxygen. For instance, infants born prematurely require extensive administration of oxygen since their lungs have incompletely formed.

Cannulas are used to deliver a stream of oxygen to the nasal passages of such patients. One style of a nasal cannula includes two nasal extensions which are inserted into the nostrils of the patient. For instance, U.S. Pat. No. 4,106,505 issued to Salter et al., U.S. Pat. No. 5,188,101 issued to Tumolo, and U.S. Pat. No. 5,271,391 issued to Graves all relate to nasal cannulas having invasive nasal extensions. A benefit of the invasive nasal extension is that substantially the entire oxygen stream is delivered to the nasal passages of the patient.

Several disadvantages are associated with the nasal cannulas having invasive nasal extensions. For example, the nasal extensions tend to dry out the nasal membranes of the patient, particularly patients who require extensive administration of oxygen, such as premature babies. The nasal extensions tend to get clogged with nasal mucus which reduces the supply of oxygen to the patient. The nasal extensions tend to pop out of the patient's nostrils during sleep removing the entire stream of oxygen from the nostrils of the patient. The shape of the nasal cannula with nasal extensions makes them difficult to clean. The invasive nasal extensions are intimidating to pediatric patients who will often tend to pull the nasal extensions from their noses. A nurse or care giver will often have to reapply the invasive nasal cannula. This can cause the patient discomfort since realigning the nasal cannula will require re-taping of the patient's face to hold the tubes in place.

To overcome the disadvantages associated with a nasal cannula having nasal extensions, a nasal cannula which is non-invasive, i.e. not having nasal extensions extending into the nostrils of the patient, is disclosed in U.S. Pat. No. 4,406,283 issued to Bir. This patent relates to a non-invasive nasal cannula having no portion which intrudes into the nostrils or other sensitive parts of the patient's face. The Bir cannula comprises a piece of flexible tubing having a plurality of apertures. The apertures are circumferentially spaced along the tubing so as to develop a number of ejecting streams of oxygen, at least some of which are directed upwardly and into the region of the nose so that the patient can readily receive an atmosphere of virtually pure oxygen.

There are several advantages to the structure of a non-invasive cannula. For instance, the non-invasive cannula is more comfortable to the patient since the cannula will not dry out the nasal membranes of the patient. The apertures of the non-invasive nasal cannula are less likely to become clogged with nasal mucus, and during sleep there is nothing to disengage from the patient's nose to prevent the oxygen supply from reaching the patient. The non-invasive nasal cannula is less intimidating to pediatric patients so that such a patient tends to leave the non-invasive cannula alone and not pull it away from their face. The non-invasive cannula is care giver friendly since it is easier to line up and allows some leeway in placement which prevents the re-taping of the patient's face to position the cannula.

A major disadvantage of the Bir non-invasive nasal cannula is that only a small percentage of the oxygen stream actually is delivered to the patient's nasal passages. For instance, the plurality of apertures in the Bir cannula allow the oxygen to escape at several angles relative to the patient. Much of the oxygen is vented away from the patient's nasal passages.

Although the aforementioned nasal cannula may function satisfactorily for its intended purpose, there is a need for a non-invasive nasal cannula having all the benefits stated above of a non-invasive cannula but also which directs substantially the entire stream of oxygen toward the patient's nasal passages. The improved non-invasive nasal cannula should be easy to position on the patient's face and have means for remaining in a correct position. The improved non-invasive nasal cannula should make it easy for a care giver to visualize whether the cannula is clean and supplying an appropriate amount of oxygen, and it should be easy to clean if it should become partially or fully clogged. Finally, an improved non-invasive nasal cannula should be especially adapted for use on premature infants to allow a stream of oxygen to be administered to the infant while allowing the infant to be comfortable.

OBJECTS OF THE INVENTION

With the foregoing in mind, a primary object of the present invention is to provide an improved non-invasive nasal cannula which directs substantially the entire stream of oxygen towards the nasal passages of the patient.

Another object of the present invention is to provide a non-invasive nasal cannula which is comfortable to the patient.

A further object of the present invention is to provide a nasal cannula which is easy to visually inspect for clogging and which is easy to clean.

A still further object of the present invention is to provide a non-invasive nasal cannula which will maintain its proper placement above the upper lip of the patient and below the patient's nasal passages.

SUMMARY OF THE INVENTION

More specifically, the present invention provides a non-invasive nasal cannula for use with an oxygen supply to deliver a stream of oxygen to a patient's nasal passages. The cannula has an elongate body extending along a longitudinal axis and terminating in opposite end portions. At least one of the opposite end portions has an opening for receiving the stream of oxygen from the oxygen supply. The elongate body has an elongate orifice for delivering the stream of oxygen to the patient's nasal passages. The elongate orifice extends along the longitudinal axis of the cannula.

The cannula has means integral with the elongate body for directing substantially the entire stream of oxygen toward the patient's nasal passages. The cannula also has a positioning flange integral with the elongate body for positioning the elongate body in a proper position on the patient. The positioning flange disposes the elongate orifice adjacent the patient's nasal passages and helps to retain it in this position during oxygen therapy.

BRIEF DESCRIPTION OF THE DRAWINGS

The foregoing and other objects, features and advantages of the present invention should become apparent in the following description when taken in conjunction with the accompanying drawings, in which:

FIG. 1 is a perspective view of a young patient receiving a supply of oxygen from an improved non-invasive nasal cannula embodying the present invention;

FIG. 2 is a perspective view of one embodiment of an improved non-invasive nasal cannula according to the present invention;

FIG. 3 is a transverse cross-sectional view taken along line 3—3 of FIG. 2;

FIG. 4 is a cross-sectional view of an alternate embodiment of an improved non-invasive nasal cannula;

FIG. 5 is a perspective view of the most preferred embodiment of a non-invasive nasal cannula according to the present invention; and FIG. 6 is a cross-sectional view taken along line 6—6 of FIG. 5.

DETAILED DESCRIPTION OF PREFERRED EMBODIMENTS

Referring now to the drawings, FIG. 1 illustrates a young patient being administered a pure supply of oxygen. A nasal cannula 10 is located above the patient's upper lip and adjacent the patient's nasal passages. The nasal cannula 10 has a horizontally-elongate body 24 which is connected to a source of oxygen (not shown) in a loop system whereby both end portions, 12 and 14, of the cannula are provided with a stream of oxygen. A pair of flexible tubing, 16 and 18, delivers the oxygen to the opposite end portions 12 and 14 of the cannula, the tubing 16 and 18 being connected to a source of oxygen (not shown). The cannula 10 is held on the face of the patient by affixing the flexible tubes 16 and 18 to the cheeks of the patient with pressure sensitize adhesive tape 20.

The improved non-invasive nasal cannula 10 of the present invention utilizes a single, oversized orifice 22 extending longitudinally on one side of the elongate body 24 of the cannula 10. The single orifice 22 is disposed horizontally below and adjacent the patient's nasal passages to deliver the stream of oxygen to the nasal passages. The use of the oversized orifice 22 to deliver oxygen eliminates the need for nasal extensions to be placed in the nostrils of the patient. The enlarged orifice 22 is easy to visually check by a care giver to determine whether the cannula 10 is clogged with nasal mucus. The oversized orifice 22 also makes it easy for the care giver to clean the cannula 10 should it become clogged or partially clogged. Also, since the orifice 22 is located on only one side of the elongate cannula body 24, the stream of oxygen is directed only toward the nasal passages and not in any other direction.

The improved non-invasive nasal cannula 10 of the present invention includes a means 26 to direct substantially the entire stream of oxygen toward the patient's nasal passages. As best seen in FIGS. 3, 4 and 6, the means 26 is located adjacent a distal side 32 of the orifice 22 and is designed to extend substantially toward but not upwardly beyond the tip of the patient's nose. In the preferred embodiment shown in FIG. 5, the elongate body 24 of the cannula 10 has an enlarged central portion 28 extending between the two smaller diameter end portions 12 and 14. The central portion 28 provides a raised ridge, or lip, 30 which directs the flow of the oxygen toward the nasal passages on the patient's nose. In FIG. 6, the raised ridge 30 provides the oxygen directing means and prevents the oxygen stream from escaping up over the top of the nose and away from the patient's nasal passages.

An alternate means 26 to direct the flow of oxygen towards the patient's nasal passages is shown in an embodiment of the present invention in FIG. 2. In this embodiment, an upstanding flange 34 extends from the elongate body such that it can deflect the stream of oxygen back toward the patient's nasal passages. Alternatively, the flange 34 could be angled toward the patient as shown in FIG. 4.

Another feature of the improved non-invasive nasal cannula 10 of the present invention is a positioning flange 36. The positioning flange 36 is located adjacent a proximal side 38 of the orifice 22. The positioning flange 36 contacts and rests on the patient's face above the patient's upper lip and below the patient's nasal passages. The positioning flange 36 has a smooth flat bottom portion 40 for contacting the patient's skin. The smooth flat shape prevents the cannula from rolling or twisting on the patient's face, thereby maintaining the single orifice 22 disposed adjacent the nasal passages of the patient. An alternate embodiment of a positioning flange 36, illustrated in FIGS. 2 and 3, also acts to prevent displacement of the cannula 10 on the patient's face.

The improved non-invasive nasal cannula 10 described herein provides a nasal cannula having all the benefits of a non-invasive nasal cannula but with the improvement that substantially the entire oxygen stream is being vented toward the patient's nasal passages as does a nasal cannula having nasal extensions. The improved non-invasive nasal cannula allows a patient which requires a significant amount of oxygen administration, such as premature babies, to have such oxygen in a comfortable manner. As the patient's comfort increases, the effectiveness of the oxygen being supplied to the patient increases because the comfort eliminates the patient's pulling the cannula away from the face.

By way of example, and not by way of limitation, the elongate body 24 of the cannula 10 can have a lengthwise dimension of approximately two inches and a widthwise dimension at the end portions 12 and 14 of approximately one-quarter inch. The elongate body 24 illustrated at FIG. 5 can have a widthwise dimension at its central portion 28 of approximately double that of its end portions 12 and 14. The orifice 22 can have a lengthwise dimension of approximately 1¼ inches and a widthwise dimension in the range of approximately ⅛ to ⅜ inches. The means 26 of FIG. 2 can have a lengthwise dimension of approximately 1½ inches and extend radially from the elongate body 24 approximately ⅜ inch. The positioning flange 36 can have a lengthwise dimension equal to that of means 26 and extend radially from the elongate body 24 in a range of approximately ⅛ to ⅜ inch. The smooth flat bottom portion 40 of positioning flange 36 can have a widthwise dimension in a range of 1/16 to ⅛ inch.

While preferred non-invasive nasal cannulas in the illustrated embodiments have the aforementioned specific dimensional and other characteristics, variations are possible.

Some of the many advantages of the present invention should now be readily apparent. For instance, the combination of a singular oversized orifice 22, a means 26 for directing the stream of oxygen solely toward the nasal passages, and a means 34 for preventing radial movement of the cannula body such that the orifice always remains disposed to the nasal passages, has improved the art of nasal cannula assemblies.

While preferred embodiments of the present invention have been described in detail, various modifications, alterations, and changes may be made without departing from the spirit and scope of the invention as defined in the appended claims.

I claim:

1. A non-invasive nasal cannula for use with an oxygen supply to deliver a stream of oxygen to a patient's nasal passages, comprising:
   an elongate body extending along a longitudinal axis and terminating in opposite end portions;
   at least one of said opposite end portions having an opening for receiving the stream of oxygen;
   said elongate body having an elongate orifice for delivering the stream of oxygen to the patient's nasal passages, said elongate orifice extending along said longitudinal axis;
   means integral with said elongate body for directing the stream of oxygen toward the patient's nasal passages, said means extending substantially toward but not upwardly beyond the tip of the patient's nose; and
   a positioning flange integral with said elongate body for positioning said elongate body in a proper position on the patient such that said elongate orifice remains disposed adjacent the patient's nasal passages.

2. A non-invasive nasal cannula according to claim 1, wherein said elongate orifice has a distal side and a proximal side, and wherein said means is located adjacent said distal side of said elongate orifice, whereby a portion of the oxygen stream which would otherwise escape above the patient's nose will be deflected toward the patient's nasal passages.

3. A non-invasive nasal cannula according to claim 2, wherein said means extends the entire length of said distal side of said elongate orifice.

4. A non-invasive nasal cannula according to claim 3, wherein said means comprises a top ridge of said elongate body which forms said distal side of said elongate orifice.

5. A non-invasive nasal cannula according to claim 3, wherein said means comprises a flange extending from said elongate body.

6. A non-invasive nasal cannula according to claim 5, wherein said flange extends radially from said elongate body and axially therealong.

7. A non-invasive nasal cannula according to claim 3, wherein said positioning flange extends from said elongate body adjacent said proximal side of said elongate orifice.

8. A non-invasive nasal cannula according to claim 7, wherein said positioning flange extends radially from said elongate body and axially therealong.

9. A non-invasive nasal cannula according to claim 8, wherein said positioning flange has a smooth, flat edge for resting against the patient's upper lip.

10. A non-invasive nasal cannula according to claim 9, wherein said elongate body is made of a flexible material.

11. An improved non-invasive nasal cannula for delivering oxygen to a patient's nasal passages, the cannula having a flexible elongate body connected to a source of oxygen, the improvement wherein:
    the elongate body has formed therein an elongate orifice with a distal side and a proximal side, said elongate orifice providing a passageway for oxygen to the patient's nasal passages when said elongate orifice is disposed adjacent to the patient's nasal passages;
    means integral with the elongate body and adjacent to said distal side of said elongate orifice for directing the oxygen toward the patient's nasal passages, said means extending substantially toward but not upwardly beyond the tip of the patient's nose; and
    a positioning flange integral with the elongate body and adjacent to said proximal side of said elongate orifice, said positioning flange having a smooth, flat free edge.

12. An improved non-invasive nasal cannula according to claim 11, wherein said means comprises a top ridge of said elongate body which forms said distal side of said elongate orifice.

13. An improved non-invasive nasal cannula according to claim 11, wherein said means comprises a flange extending from said elongate body lengthwise alongside said elongate orifice for directing oxygen therefrom.

14. A non-invasive nasal cannula for delivering a source of oxygen to a premature baby's nasal passages in a comfortable manner for the premature baby, comprising:
    an elongate body extending along a longitudinal axis and terminating in opposite end portions, each of said opposite end portions receiving the stream of oxygen, said elongate body having an orifice extending along said longitudinal axis, said orifice having a distal side and a proximal side;
    means integral with the elongate body and adjacent to said distal side of said elongate orifice for directing substantially the entire stream of oxygen exiting said elongate body via said orifice toward the premature baby's nasal passages, said means extending substantially toward but not upwardly beyond the tip of the patient's nose; and
    a positioning flange integral with said elongate body and adjacent to said proximal side of said orifice, said positioning flange having a smooth, flat free edge for placement on a face of the premature baby so that said orifice remains disposed adjacent the nasal passages.

15. A non-invasive nasal cannula according to claim 14, wherein said means comprises a top ridge of said elongate body which forms said distal side of said orifice.

16. A non-invasive nasal cannula according to claim 15, wherein said opposite end portions of said elongate body have a smaller cross-section dimension than a central portion of said elongate body at said top ridge.

17. A non-invasive nasal cannula according to claim 16, wherein said central portion of said elongate body at said top ridge has a cross-section dimension approximately double said cross-section dimension of said opposite end portions.

18. A non-invasive nasal cannula according to claim 17, wherein said smooth, flat free edge of said positioning flange has a widthwise dimension in a range of approximately $\frac{1}{16}$ to $\frac{1}{8}$ inch.

19. A non-invasive nasal cannula according to claim 14, wherein said means comprises a flange extending from said elongate body.

20. A non-invasive nasal cannula according to claim 19, wherein said flange extending from said distal side of said orifice is angled toward said premature baby.

* * * * *